United States Patent [19]

Lemal et al.

[11] 3,987,063
[45] Oct. 19, 1976

[54] PROCESS FOR THE PRODUCTION OF MALEIC ANHYDRIDE FROM BUTANE

[75] Inventors: René Lemal, Obourg; Jacques Vekemans, Brussels, both of Belgium

[73] Assignee: U.C.B., Societe Anonyme, Belgium

[22] Filed: July 31, 1974

[21] Appl. No.: 493,621

[30] Foreign Application Priority Data
Aug. 3, 1973  United Kingdom............... 36943/73

[52] U.S. Cl............................. 260/346.8 A; 252/437
[51] Int. Cl.²................................... C07D 307/60
[58] Field of Search................................. 260/346.8

[56] References Cited
UNITED STATES PATENTS 3,156,705  11/1964  Kerr................................. 260/346.8
3,856,824  12/1974  Raffelson et al................. 260/346.8
3,862,146  1/1975  Boghosian........................ 260/346.8
3,888,886  6/1975  Young et al...................... 260/346.8

FOREIGN PATENTS OR APPLICATIONS
40-7888  4/1965  Japan............................... 260/346.8

Primary Examiner—Henry R. Jiles
Assistant Examiner—Bernard Dentz
Attorney, Agent, or Firm—Wenderoth, Lind & Ponack

[57] ABSTRACT

Process for the manufacture of maleic anhydride which comprises contacting in the vapor phase a mixture of butane and molecular oxygen with a catalyst comprising in chemical combination phosphorus, vanadium, oxygen and at least one metal activator selected from the group consisting of cobalt, nickel and cadmium as well as said catalyst used in this process.

10 Claims, No Drawings

PROCESS FOR THE PRODUCTION OF MALEIC ANHYDRIDE FROM BUTANE

The present invention relates to the production of maleic anhydride by catalytic oxidation of butane in the vapor phase by means of molecular oxygen, and to the catalysts used in this process.

Until quite recently the raw material used for the production of maleic anhydride was exclusively benzene. In view of the scarcity and cost of this raw material, it is at present being attempted to replace it by other hydrocarbons derived from petroleum, particularly butane. Butane however is difficult to oxidize into maleic anhydride, and it is only recently that catalysts have been specially developed for this synthesis.

Thus, Belgian Patent Specifications No. 791,770 and 801,138 describe the preparation of catalysts which are composed of phosphorus and vanadium in an oxidized form, whose activity in the oxidation of butane into maleic anhydride enables practical application to be expected. However, the production of these catalysts is delicate, because they must undergo heat treatment under very precise temperature conditions and in the presence of a gaseous atmosphere the composition of which must be scrupulously respected, which is difficult to realize in an industrial plant.

Others have attempted to improve the activity of P/V catalysts by adding activators to them. Thus, in German Patent Application D.O.S. No. 2,248,746 P/V/Fe catalysts are described in which the P/V ratio is from 1 to 20 atoms of P per atom of V and in which the Fe/V ratio is from 0.2 to 10 atoms of Fe per atom of V. However, the yields of maleic anhydride remain rather low and do not attain 30% by weight. Belgian Patent No. 791,294 describes the use of catalysts of the P/V type in which zinc, copper, bismuth, or lithium are added as activator, the ratios P/V/ activator being respectively 0.05–5 atoms/1 atom/0.05–0.5 atom.

The Applicants have carried out research work to ascertain whether other elements do not exist which are capable of being used as activators for V/P catalysts intended for the oxidation of butane into maleic anhydride. This work has shown that cobalt, nickel, and cadmium can also be used very advantageously for this purpose and that the catalysts prepared according to this invention do not require any particular thermal treatment.

Consequently, the present invention relates to a process for the production of maleic anhydride which comprises contacting in the vapor phase a mixture of butane and molecular oxygen with a catalyst comprising in chemical combination phosphorus, vanadium, oxygen and at least one metal activator selected from the group consisting of cobalt, nickel and cadmium. More particularly, the catalyst used according to the invention has an atomic ratio of phosphorus to vanadium of 0.5:1 to 3:1 and an atomic ratio of metal activator to vanadium of 0.05:1 to 0.5:1.

Phosphorus compounds which can be used for the preparation of catalysts according to the invention are phosphorus pentoxide, ortho-, meta-, pyro-, tri-, or polyphosphoric acids or their ammonium salts, phosphorus oxychloride, phosphorus tri- or pentachloride, cobalt phosphate, nickel phosphate, cadmium phosphate, etc.

Vanadium tri- or pentoxide, vanadyl mono-, di-, or trichloride, ammonium metavanadate, vanadium phosphate, meta- or pyrovanadic acid, vanadium oxalate, etc., may be mentioned as vanadium compounds suitable for the preparation of the catalysts.

Cobalt, nickel, and cadmium compounds used for introducing these elements into the catalysts of the present invention are the oxides, hydroxides, salts such as the carbonate, chloride, nitrate, oxalate, etc.; they may also already contain phosphorus and/or vanadium and may for example be in the form of cobalt, nickel, and/or cadmium phosphates, vanadates, phosphovanadates, etc. It is even possible to contemplate the use of cobalt, nickel, and/or cadmium in elementary form, provided that they are converted into salts under the conditions of preparation of the catalysts.

The catalyst according to the invention may be prepared by dissolving a vanadium compound in a solvent such as water or an aliphatic monhydric alcohol having 1 to 4 carbon atoms by means of an acid such as hydrochloric acid, oxalic acid or any acid that volatilizes during the calcination of the catalyst.

Depending on the vanadium compound and the solvent used, heating or cooling for a variable time might be necessary to bring about the dissolution.

The activator (cobalt, nickel and/or cadmium or their compounds) may be added at the same time as the vanadium compound or after dissolution of the latter.

The phosphorus compound is preferably added after dissolution of both the vanadium compound and the activator. The mixture is then heated under reflux for ½ to 7 hours, the solvent is evaporated and the solid residue is dried. This dry residue constitutes the catalyst.

If the catalyst according to the invention is used without a support, the solid residue is eventually ground, and formed into pastilles having a dimension of about 1 to 9 mm for fixed bed catalysis. If the catalyst is used in fluidized bed, the solid residue is ground into particles of from 10 to 150 microns.

However, the catalyst according to the invention may also be used on a support. The latter may for example be silica, alumina, silicon carbide, kieselguhr, etc. For the preparation of the catalysts according to the invention which rest on a support, the latter may be added to the catalytic mixture at the commencement of the preparation of the mixture, or at any stage in the course of its preparation. The catalyst may also be deposited on the support after the termination of the preparation of the catalyst, when the latter still contains the solvent used as reaction medium, followed by evaporation of the solvent. Provision may also be made for mixing the catalyst and support in the dry state, and compressing the mixture to form pastilles. Supported catalysts according to the invention should have the particle dimensions indicated above for the purposes of fixed bed or fluidized bed catalysis.

The weight ratio between the catalyst and the catalyst support may vary between 5:95 and 95:5.

The butane which is to be converted into maleic anhydride by the catalytic process of the invention may be chemically pure n-butane or, for obvious economic reasons, technical butane. The latter will preferably have as high as possible an n-butane content, for example 90% or more; as a rule the substances accompanying technical butane, such as for example isobutane, propane, butenes, etc., do not hinder the conversion of n-butane into maleic anhydride in the process of the invention.

The gas containing molecular oxygen which is used for the catalytic oxidation of butane may be any gas containing molecular oxygen, preferably air. The air may by anhydrous or it may contain a certain amount of water vapor, for example the amount of water vapor corresponding to its natural hygrometric degree under ambient conditions.

No restrictions are imposed with regard to the nature of the apparatus for carrying out the invention. Any traditional reactors used for fixed bed catalysis may be employed, for example mono- or multitubular reactors, or for fluidized bed catalysis, for example reactors in which the fluidized bed is of the descending, ascending, or stationary type. The material of the reactors may be any of the materials normally used, since there are here no acute problems of corrosion. It will therefore be possible for the material used to be mild steel, steel having a higher carbon content, alloy steels, such as for example stainless steel, etc.

In the process according to the invention for the production of maleic anhydride from butane, a gaseous mixture of butane and a gas containing molecular oxygen, preferably air, is passed over the catalyst according to the invention at a reaction temperature of 350°–550° C; if desired, the air and butane may be preheated, either separately or mixed together before reaching the reaction zone. The volumetric ratio between the air and the butane must be so selected as to fall outside explosibility limits. As a rule, in the case of fixed bed catalysis, 1–2% by volume of butane is used per 99–98% by volume of air; in the case of fluidized bed catalysis 1–4% by volume of butane is used per 99–96% by volume of air. The reaction may be carried out under normal pressure or preferably under a higher pressure in order at least to compensate for the losses of head undergone by the gaseous reaction mixture passing through the production apparatus; for this reason the reaction pressure will advantageously be between 0.1 and 10 kg/cm$^2$ gauge. The contact time between the butane/air mixture and the catalyst according to the invention varies from 0.5 to about 4 seconds, the contact time being calculated under normal conditions of temperature (0° C) and pressure (760 mm Hg). On leaving the reactor the gaseous mixture is treated to recover maleic anhydride in the traditional manner, for example by condensation, by adsorption on solids, or by adsorption in a liquid solvent, such as water or a suitable organic solvent.

The following examples illustrate the invention without limiting it.

EXAMPLE 1

This example describes the preparation in aqueous medium of a P/V/O catalyst used as control, and also the preparation of activated catalysts according to the invention.

65.1 parts by weight of vanadium pentoxide are dissolved under reflux in 1,000 parts of concentrated hydrochlorid acid. After heating for 4 hours under reflux, the activator is added, boiling under reflux is continued for 2 hours and phosphoric acid is added. Boiling under reflux is continued for a further period of 6 hours, then the solution is evaporated to dryness. The solid residue is dried at 120° C for 12 hours, coarsely crushed, then heated at 350° C for 4 hours. After cooling the residue is ground and screened with a screen of 36 mesh per cm. Sufficient graphite is added to the powder to ensure that the mixture contains 1% by weight thereof, and the mixture is compressed into 9 mm pastilles. The pastilles are crushed; the fraction passing through a screen with an opening of 1.6 mm and retained on a screen with an opening of 1 mm constitutes the charge of the reactor.

Table I below shows the amount and nature of the activator used and the amount of phosphoric acid added per 65.1 parts by weight of vanadium pentoxide.

TABLE I

| Catalyst No. | Nature of activator | Parts by weight of activator | Parts by weight of phosphoric acid | Atomic ratio of elements in the catalyst |
| --- | --- | --- | --- | --- |
| 1 a | none | — | 80.1 | 1 V : 1.14 P |
| 1 b | CoCl$_2$.6 H$_2$O | 32.3 | 80.1 | 1 V : 1.14 P : 0.19 Co |
| 1 c | CoCl$_2$.6 H$_2$O | 17.05 | 80.1 | 1 V : 1.14 P : 0.1 Co |
| 1 d | CdCl$_2$.2.5 H$_2$O | 16.34 | 80.1 | 1 V : 1.14 P : 0.1 Cd |
| 1 e | CdCl$_2$.2.5 H$_2$O | 8.17 | 80.1 | 1 V : 1.14 P : 0.05 Cd |
| 1 f | NiCl$_2$.6 H$_2$O | 32.30 | 80.1 | 1 V: 1.14 P : 0.19 Ni |
| 1 g | CoCl$_2$.6 H$_2$O | 42.54 | 80.1 | 1 V : 1.14 P : 0.25 Co |
| 1 h | CoCl$_2$.6 H$_2$O | 32.30 | 77.3 | 1 V : 1.10 P : 0.19 Co |

EXAMPLE 2

This Example describes the preparation in alcoholic medium of a P/V/O catalyst used as control and also the preparation of activated catalysts according to the invention.

In 1000 parts by weight of solvent, 227.35 parts by weight of vanadium pentoxide and the desired amount of the metal activator compound are suspended. By means of a plunging tube, 330 parts by weight of dry gaseous hydrogen chloride are added at such a speed that the temperature does not exceed 40° C. The vanadium pentoxide dissolves.

On the other hand, the desired amount of phosphoric acid is dissolved in 250 parts by weight of the solvent.

The first solution is added to the second and the mixture is boiled under reflux for 90 minutes. The solvent is evaporated and the solid residue dried at 150° C. for 6 hours.

After cooling, the residue is ground, screened and formed into pastilles as in Example 1. The pastilles are crushed and the fraction of 1 to 1.5 mm constitutes the charge of the reactor.

Table II below gives the amount and nature of the activator used, the nature of the solvent and the amount of phosphoric acid used per 227.35 parts by weight of vanadium pentoxide.

TABLE II

| Catalyst No. | Nature of solvent | Nature of activator | Parts by weight of activator | Parts by weight of H₃PO₄ | Atomic ratio of elements in the catalyst |
|---|---|---|---|---|---|
| 2 a* | isobutanol | none | — | 294.1 | 1 V : 1.2 P |
| 2 b | isobutanol | CoCl₂.6 H₂O | 113.05 | 279.3 | 1 V : 1.14 P : 0.19 Co |
| 2 c | methanol | CoCl₂ | 81.15 | 279.3 | 1 V : 1.14 P : 0.25 Co |
| 2 d | methanol | CoCl₂ | 61.70 | 279.3 | 1 V : 1.14 P : 0.19 Co |

*catalyst according to Belgian Patent No. 801,138.

The following Examples 3 and 4 give the yields obtained by means of the catalysts of the invention.

The catalyst is placed in a microreactor made of glass having an interior diameter of 8 mm and having a thermometer shaft with an outer diameter of 4 mm. The volume of the catalyst is 4.15 ml.

The contact time is equal to the ratio of the volume of the catalyst to the rate of flow of the air-butane mixture, calculated in ml/second under normal conditions of temperature and pressure (0° C. and 760 mm Hg).

The yield of maleic anhydride is equal to the ratio, multiplied by 100, of the weight of the maleic anhydride produced to the weight of butane fed.

EXAMPLE 3

This Example shows that the mean yields obtained by means of the activators according to the invention are equal to or higher than the best yield obtained in the Belgian Patent No. 791,294.

In this patent, the best yield is 94% but at a temperature of 476° C and with a contact time of 4.09 seconds (expressing the results of this Patent under normal conditions of temperature and pressure).

TABLE III

| Catalyst No. | Temperature (° C.) | Contact time (seconds) | Yield (%) |
|---|---|---|---|
| 1 a | 450 | 1.9 | 50 |
| 1 b | 450 | 1.9 | 92.4 |
| 1 c | 480 | 1.9 | 76 |
| 1 d | 480 | 1.9 | 78.6 |
| 1 e | 490 | 1.9 | 85.2 |
| 1 f | 440 | 1.9 | 88 |
| 1 g | 453 | 1.9 | 72.7 |
| 1 h | 431 | 2.5 | 77.7 |
| 2 a | 405 | 3.5 | 93.5 |
| 2 b | 387 | 3.5 | 100 |
| 2 c | 410 | 3.5 | 93 |
| 2 d | 405 | 3.5 | 101.4 |
| 2 d | 432 | 1.8 | 96.4 |

EXAMPLE 4

This Example shows that the addition of the activator of the invention allows the omission of the laborious thermal treatment exacted for the vanadium-phosphorus catalysts described in Belgian Patents No. 791,770 and 801,138.

The thermal treatment A described in Belgian Patent No. 791,770 consists in heating the catalyst in air at a space velocity of 120 volumes of air/volume catalyst/hour at 385° C., and maintaining this temperature for 1 hour. Temperature is then raised to 414° C. in an air-butane atmosphere (containing 1.5% by volume of butane) at a velocity of 120 volumes of this mixture/volume catalyst/hour. Space velocity is then increased to 700 volumes/volume/hour, while heating the catalyst gradually to 470° C at the rate of 5° to 10° C. per hour.

The thermal treatment B, described in Belgian Patent No. 801,138, consists in heating the catalyst to 380° C. at the rate of 3° C./minute in a stream of air at the rate of flow of 1.5 volumes air/volume catalyst/minute. This temperature is kept for 2 hours, then it is raised from 380° to 480° C at the rate of 3° C./minute while passing a stream of air-butane (containing 1.5% by volume of butane) at the rate of flow of 1.5 volumes gas mixture/volume catalyst/minute. The temperature of 480° C. and the rate of flow of the air-butane mixture are maintained for 16 hours. The temperature is then lowered to 420° C. while raising the rate of flow to 17 volumes/volume/minute. The temperature is then adjusted so as to obtain a conversion of butane of 90%.

The catalysts that do not undergo a thermal treatment are subjected from room temperature onwards to a rate of flow of the air-butane mixture (containing 1.5% by volume of butane) which is calculated in such a manner as to obtain the desired contact time, while raising the temperature as quickly as ever possible for the micro-reactor.

TABLE IV

| Catalyst No. | Thermal treatment | Yield (%) | Contact time (seconds) | Temperature (° C.) |
|---|---|---|---|---|
| 1 b | A | 91 | 1.9 | 460 |
| 1 b | none | 92.4 | 1.9 | 460 |
| 1 b | B | 20.3 | 3.5 | 420 |
| 1 b | none | 84 | 3.5 | 420 |
| 2 b | B | 22.6 | 3.5 | 400 |
| 2 b | none | 100 | 3.5 | 387 |
| 2 a | B | 93.5 | 3.5 | 405 |
| 2 a | none | 84.5 | 3.5 | 460 |

I claim:

1. A process for the production of maleic anhydride which comprises contacting at a temperature of from about 350° to about 550° C a mixture of butane and molecular oxygen with a catalyst consisting essentially of phosphorus, vanadium, oxygen and at least one metal activator selected from the group consisting of cobalt, nickel and cadmium, said catalyst having an atomic ratio of phosphorus to vanadium of 0.5:1 to 3:1 and an atomic ratio of said metal activator to vanadium of 0.05:1 to 0.5:1.

2. A process of claim 1, wherein the activator is cobalt.

3. The process of claim 1, wherein the activator is nickel.

4. the process of claim 1, wherein the activator is cadmium.

5. The process of claim 1, wherein the catalyst is supported.

6. The process of claim 1, wherein the butane is technical butane having an n-butane content of at least 90%.

7. The process of claim 1, wherein the butane is pure n-butane.

8. The process of claim 1, wherein a fixed bed catalyst is used and the mixture contacted with the catalyst contains 1–2% by volume of butane per 99–98% by volume of air.

9. The process of claim 1, wherein a fluid bed catalyst is used and the mixture contacted with the catalyst contains 1–4% by volume of butane per 99–96% by volume of air.

10. The process of claim 1, wherein the catalyst used is prepared by dissolving a vanadium compound in a solvent selected from the group consisting of water and an aliphatic monohydric alcohol having 1 to 4 carbon atoms by means of a volatilizable acid, adding at least one compound of a metal selected from the group consisting of cobalt, nickel and cadmium during or after the dissolution of the vanadium compound, adding a phosphorus compound after dissolution is complete, heating the mixture thus obtained at reflux temperature during ½ to 7 hours, evaporating the solvent and thereby drying the resulting residue.

\* \* \* \* \*